United States Patent

Pekka

[19]

[11] Patent Number: 5,964,219
[45] Date of Patent: Oct. 12, 1999

[54] METHOD AND ARRANGEMENT FOR PROCESSING RESPIRATORY GAS OF AN INTUBATED PATIENT

[75] Inventor: Meriläinen Pekka, Helsinki, Finland

[73] Assignee: Instrumentarium Oy, Helsinki, Finland

[21] Appl. No.: 08/877,868

[22] Filed: Jun. 18, 1997

[30] Foreign Application Priority Data

Jun. 27, 1996 [FI] Finland ................................ 962655

[51] Int. Cl.⁶ ................................................ H61M 16/00
[52] U.S. Cl. ................................ 128/203.16; 128/203.12; 128/207.17; 128/205.11; 128/205.12
[58] Field of Search ................ 128/203.12, 203.17, 128/205.11, 205.14, 205.28, 207.14, 204.23, 204.17, 203.16, 205.12; 600/532, 538, 540

[56] References Cited

U.S. PATENT DOCUMENTS

| | | | |
|---|---|---|---|
| 4,425,914 | 1/1984 | Ray et al. ................ | 128/203.12 |
| 4,516,573 | 5/1985 | Gedeon . | |
| 4,819,629 | 4/1989 | Jonson . | |
| 4,821,709 | 4/1989 | Jensen ................ | 128/205.11 |
| 4,829,998 | 5/1989 | Jackson ................ | 128/203.17 |
| 5,088,332 | 2/1992 | Meriläinen et al. . | |
| 5,172,686 | 12/1992 | Anthony ................ | 128/203.16 |
| 5,349,946 | 9/1994 | McComb ................ | 128/203.16 |
| 5,423,313 | 6/1995 | Olsson et al. ................ | 128/203.14 |
| 5,429,123 | 7/1995 | Shaffer et al. ................ | 128/204.23 |
| 5,460,172 | 10/1995 | Eckerbom ................ | 128/201.13 |

FOREIGN PATENT DOCUMENTS

| | | |
|---|---|---|
| 243 259 | 10/1987 | European Pat. Off. . |
| 2148127 | 5/1985 | United Kingdom ............ 128/203.17 |
| 2297914 | 8/1996 | United Kingdom . |
| 91/19527 | 12/1991 | WIPO . |

Primary Examiner—Aaron J. Lewis
Assistant Examiner—Virendra Srivastava
Attorney, Agent, or Firm—Andrus, Sceales, Starke & Sawall

[57] ABSTRACT

A method and an arrangement for processing respiratory gas of an intubated patient, wherein the level of humidity of the inhalation gas is increased, if necessary, before the gas is supplied to the patient. To provide accurate and correctly timed humidification, the patient's respiratory volume is measured, the amount of water discharged from the patient is determined on the basis of the measured respiratory volume, and a desired amount of water, dependent on the amount of water discharged from the patient, is supplied to the patient's respiratory tract during the next respiratory phase(s).

36 Claims, 1 Drawing Sheet

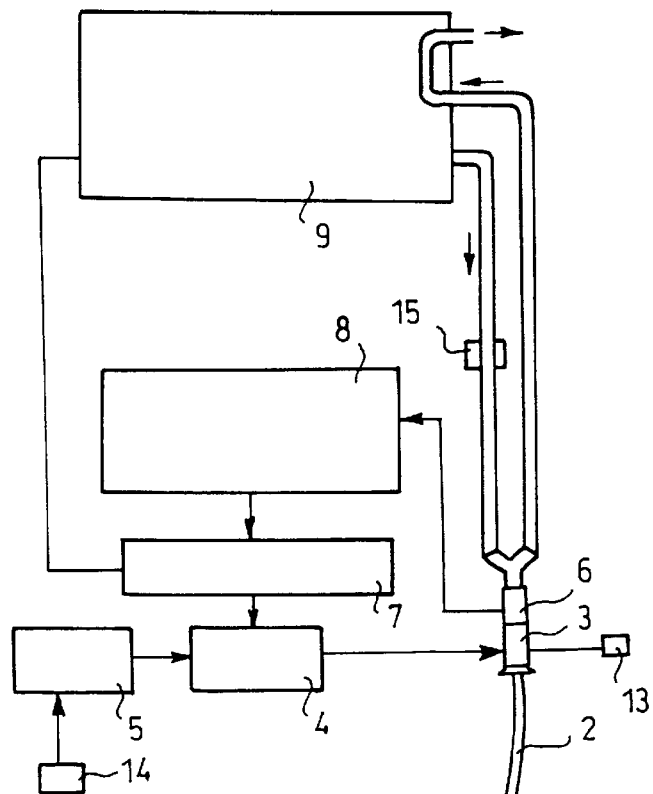
FIG. 1
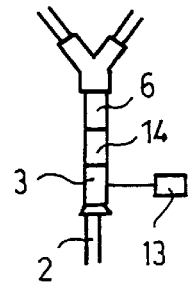
FIG. 4
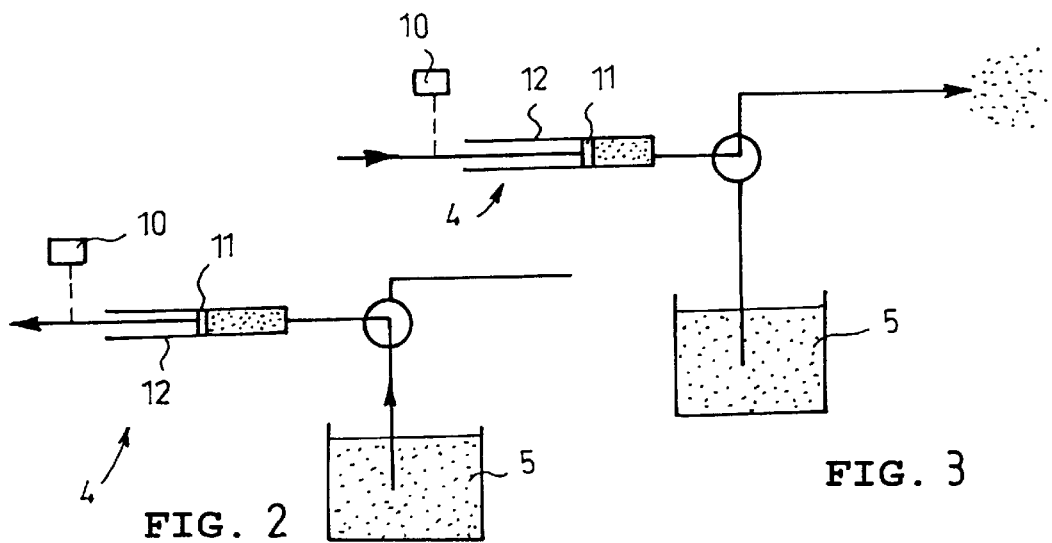
FIG. 2
FIG. 3

METHOD AND ARRANGEMENT FOR PROCESSING RESPIRATORY GAS OF AN INTUBATED PATIENT

BACKGROUND OF THE INVENTION

The invention relates to a method for processing respiratory gas of an intubated patient, wherein the humidity level of inhalation gas is raised, if necessary, before the gas is supplied to the patient. The invention also relates to an arrangement for processing respiratory gas of an intubated patient.

Respiratory gas of a patient connected to a respirator must be humidified and heated artificially since the artificial respiratory passage obtained through the insertion of a respiratory tube, i.e. through intubation, by-passes the mucous membranes of the nasal cavity where the respiratory gas becomes moist and warm during natural respiration. Dry and cold respiratory gas irritates the trachea and the bronchi and cools down the patient's body temperature.

Two principal methods have been used previously to artificially humidify respiratory gas of a patient.

The first known method is the use of active humidifiers. Active humidifiers vaporize water into the air to be inhaled from a heated container connected to the pipes on the inhalation side.

The second known method is the use of an artificial nose, i.e. a humidity and moisture exchanger (HME). The artificial nose is connected directly to the end of the respiratory tube where it recovers humidity and heat from the exhaled air and stores them for release to the next inhalation phase.

Both of the aforementioned methods are problematic. Adjustment of a simple active humidifier is based on the heating capacity and on the visual monitoring of the amount of the humidity produced in the patient's tubes. Usually the humidification is easily excessive, so that a harmful amount of water may gather in the tubes. In the aforementioned situation, the water must be removed from the tubes at regular intervals. Another problem is that the circumstances in the container of the humidifier provide an advantageous environment for the growth of bacteria. An artificial nose, in turn, can never be used to humidify excessively since only 80 to 90% of the humidity contained in the exhaled air can be recovered and utilized in the next inhalation phase. Especially patients who are in intensive care and whose secretion of mucus is heavy require additional humidity to prevent the mucus gathering in the respiratory tube from drying up. The capacity of the artificial noses is not sufficient for this. The capacity of heat recovery of the artificial noses is not always sufficient, either.

BRIEF SUMMARY OF THE INVENTION

The purpose of the invention is to provide a method with which the prior art drawbacks can be eliminated. This is achieved with the invention. The method according to the invention is characterized in that the volume of the patient's respiration is measured, the amount of water that has been discharged from the patient is determined by means of the measured respiratory volume, and a desired amount of water, dependent on the amount of water discharged from the patient, is supplied to the patient's respiratory tract during the next respiratory phase(s). The arrangement according to the invention is in turn characterized in that the arrangement further comprises a flow sensor arranged to carry out a measurement on the patient's respiratory air flow, second means arranged to calculate the respiratory volume on the basis of the performed measurement, and a control unit arranged to determine the amount of water discharged from the patient on the basis of the measured respiratory volume, and an actuator and a nozzle piece that are arranged, according to directions from the control unit, to supply an amount of water, dependent on the amount of water discharged from the patient, to the patient's respiratory tract during the next respiratory phase(s).

The advantage of the invention is that the prior art drawbacks can be eliminated effectively. The invention enables adjusting the amount of the humidity and the timing of its administration to accurately suit the needs of each patient, so that the overall result is very advantageous.

BRIEF DESCRIPTION OF THE SEVERAL VIEWS OF THE DRAWINGS

The invention will be described in greater detail below by means of a preferred embodiment described in the accompanying drawing, in which FIG. 1 is a general view of a system utilizing the method according to the invention, FIG. 2 is a general view of a possible spraying arrangement during the suction, FIG. 3 is a general view of the spraying arrangement of FIG. 2 during the spraying, and FIG. 4 shows an alternative embodiment of a detail of FIG. 1.

DETAILED DESCRIPTION OF THE INVENTION

FIG. 1 shows the characteristic features of a system utilizing the method according to the invention. Reference numeral 1 denotes a patient's lungs and reference numeral 2 a respiratory tube. Reference numeral 3 denotes a nozzle piece, numeral 4 an actuator and numeral 5 a water container. Reference numeral 6 denotes in FIG. 1 a flow sensor and reference numeral 7 a control unit. Reference numeral 8 denotes in FIG. 1 a flow monitor and reference numeral 9 a respirator.

According to the basic idea of the invention, a patient's respiratory volume, preferably the exhalation volume, is measured for example in the form of single respiratory volume or minute volume, the amount of water discharged from the patient is determined on the basis of the single respiratory volume measured from the exhalation, and a desired amount of water, dependent on the amount of water discharged from the patient, is supplied to the patient's respiratory tract for example through spraying during the next respiratory phase(s). The amount of water that is dependent on the amount of water discharged from the patient may be, for example, proportional to the amount of water discharged from the patient. The starting point is adjusting the amount of humidity and the timing of its administration to accurately suit the needs of the patient by spraying an exactly determined and timed dose of water in the form of spray or vapour to the patient's air passage during each inhalation phase, for example. The amount to be sprayed is measured by means of the flow sensor 6, and the flow monitor 8 and the control unit 7 connected thereto, in which case the flow sensor 6 carries out a measurement on the patient's respiratory air flow, the flow monitor 8 calculates the respiratory volume on the basis of the measurement, and the control unit 7 determines the amount of water that has been discharged from the patient according to the respiratory volume measured. An amount of water, dependent on the amount of discharged water determined in the aforementioned manner, is supplied to the patient for example through spraying during the next respiratory phase (s).

The sensor 6 may be, for example, a spirometric sensor described in U.S. Pat. No. 5,088,332 or in the corresponding Finnish Patent 84,757, used to measure, on the basis of a pressure difference, the single respiratory volume of the preceding exhalation period. The amount of water that has been removed from the patient can then be determined accurately by assuming that the gas arriving from the patient's lungs 1 is entirely saturated with water vapour. The amount of water discharged with a breath having a volume of one liter is typically about 30 mg or 30 mm$^3$ when the temperature of the patient's exhalation is about 34° C. If required, measurement of the temperature of the exhalation air can be arranged to be carried out preferably from the end of the intubation tube. With the timing of the spraying at a certain stage of the inhalation it is also possible to control the proportion of the humidity reaching the pulmonary alveoli and the proportion remaining in the upper air passages. In this manner it is possible not only to replace the amount of water that has been discharged but to also increase selectively the humidity in the intubation tube 2 and the trachea, if necessary, to prevent the mucus from drying. The timing signal for the spraying can be obtained for example from the flow sensor 6. Another possibility is to obtain the timing signal from a ventilator or a respirator 9. The duration of the water supply process, preferably the spraying process, and its timing during the respiration, usually at the beginning of an inhalation or exhalation phase, is determined according to the needs in each situation.

The spraying of water or water vapour to the patient's respiratory circuit can be implemented in several manners. However, there are certain conditions related to the spraying that should be taken into account when designing a preferred embodiment. In order to prevent condensation, water must be sprayed as close to the orifice of the intubation tube 2 as possible and therefore to the patient side of the flow sensor 6. This also helps avoid the harmful effect of a possible aerosol or vapour spray to the flow measurement. The spraying device, pump or the like that acts as the actuator 4 must be able to supply a desired amount of water despite the high counter pressure, produced by the respirator, that prevails in the patient circuit and that can be as high as 60 to 80 $cmH_2O$. The compliance of the water pipe leading from the spraying device to the patient circuit must be very small so that even a small batch volume of water can be discharged from the nozzle piece 3 having a small diameter so that the water does not remain for example in the flexible volume of the pipe.

FIGS. 2 and 3 show an example of a possible spraying arrangement. The arrangement comprises a water container 5 and a piston 11, positioned in a cylinder 12, that forms the actuator 4 and that is controlled by a step motor 10. The piston 11 controlled by the step motor 10 sucks an amount of water that is dependent on the single respiratory volume of the exhalation to the cylinder 12 as the patient exhales (FIG. 2), and empties the water to the respiratory tract next time the patient inhales (FIG. 3). The emptying may take place either at the beginning of the inhalation in which case all the humidity reaches the lungs 1, or at the end in which case it remains in an anatomical dead space in the upper respiratory tract and in the intubation tube 2. Since the required volume of water may be very small in order that the dosage can be kept accurate, it is probably more advantageous to use a long and thin cylinder that has a small volume and that is filled and emptied during each breath, and not a large cylinder that would be filled less often.

The respiratory air can be heated either by heating the nozzle piece 3, in which case the same devices also act as water heaters, or by means of a separate heater 15. The nozzle piece 3 may be, for example, a short metal tube that is electrically heatable and that contains in its wall a small opening through which the water is sprayed. The devices used for heating the nozzle piece 3 are denoted in the figure by means of reference numeral 13.

The water can be supplied to the air passage either in the form of aerosol or gas. Both alternatives are technically easy to arrange and it might be even clinically useful that both forms could be produced with the same apparatus. Aerosol can be especially preferable if the apparatus is also to be used to administer pharmaceuticals, such as water-soluble drugs, to the patient's respiratory system. It should be mentioned that this is normally carried out with an ultrasonic apparatus or an ejector-type apparatus that uses oxygen as the operating gas. The drawback with a gas-operated nebulizer is that the oxygen level supplied to the patient changes with the installation of the apparatus and the measurement of the patient's oxygen consumption is also seriously disturbed. A nebulizer implemented according to the principle of the present invention does not have the aforementioned drawbacks. The supply of a pharmaceutical to the water to be sprayed is shown generally in FIG. 1 by means of reference numeral 14.

FIG. 4 shows a general view of an alternative embodiment of the arrangement of FIG. 1. Like reference numerals refer to corresponding parts in FIG. 4 and in FIG. 1. In the embodiment shown in FIG. 4, between the nozzle piece 3 and the flow sensor 6 there is a component 14 comprising an artificial nose (HME) or a bacterial filter or both.

The embodiment described above is in no way intended to restrict the invention, but the invention can be modified freely within the scope of the claims. Therefore it is clear that an actuator or other details in an apparatus utilizing the invention do not have to be exactly as shown in the figures, but other kinds of arrangements are also possible.

I claim:

1. A method for treating the respiratory gas of an intubated subject, a volume of respiratory gas being inhaled by the subject during an inhalation phase of a respiratory cycle and exhaled during an exhalation phase of the respiratory cycle, the method humidifying the respiratory gas inhaled by the subject and comprising the steps of:

measuring the respiratory gas volume associated with a given respiratory cycle of the subject;

determining from the measured respiratory gas volume, the amount of water that has been discharged from the subject during the exhalation phase of the respiratory cycle; and supplying an amount of water, dependent on the amount of water discharged from the subject, to the respiratory gas volume during a subsequent respiratory cycle of the subject to humidify the inhaled respiratory gas.

2. A method according to claim 1 wherein the step of measuring the respiratory gas volume is further defined as measuring the respiratory gas volume in the exhalation phase of the respiratory cycle.

3. A method according to claim 2 wherein the step of measuring the respiratory gas volume is further defined as measuring the respiratory gas volume of a single exhalation.

4. A method according to claim 1 wherein the step of measuring the respiratory gas volume is further defined as measuring the minute respiratory gas volume.

5. A method according to claim 1 wherein the water is supplied during the inhalation phase of the respiratory cycle.

6. A method according to claim 4 wherein the water is supplied during a portion of the inhalation phase.

7. A method according to claim 6 wherein the subject has a respiratory tract extending from the trachea to the lungs along which the respiratory gas volume passes during the respiratory cycle and wherein at least one of the timing and duration of the water supply is selected so that humidified respiratory gas occupies a desired portion of the respiratory tract.

8. A method according to claim 6 wherein the water is supplied in the beginning portions of the inhalation phase.

9. A method according to claim 6 wherein the water is supplied in the end portions of the inhalation phase.

10. A method according to claim 1 wherein the amount of water supplied to the respiratory gas is proportional to the amount of water discharged from the subject during exhalation.

11. A method according to claim 1 further including the step of determining a temperature characteristic of the respiratory gas and wherein the amount of water discharged from the patient is determined on the basis of the measured respiratory gas volume and the determined temperature characteristic of the respiratory gas.

12. A method according to claim 1 wherein the flow of respiratory gas is sensed and wherein the supply of water to the respiratory gas is initiated responsive to sensed flow conditions.

13. A method according to claim 1 wherein the respiratory gas volume is provided by a respiratory gas supply and wherein the supply of water is initiated responsive to a timing signal from the respiratory gas supply.

14. A method according to claim 1 wherein the water is sprayed into the respiratory gas of the subject.

15. A method according to claim 1 wherein the water is supplied to the respiratory gas of the subject in the form of an aerosol.

16. A method according to claim 1 wherein the water is supplied to the respiratory gas of the subject in the form of water vapor.

17. A method according to claim 16 further including the step of heating the supplied water to provide the water vapor.

18. A method according to claim 17 wherein the step of heating the supplied water is further defined as heating inhaled respiratory gas into which the water is supplied.

19. A method according to claim 1 further defined as including the step of adding a medicinal agent to the water supplied to the respiratory gas.

20. A method according to claim 19 further defined as adding a water soluble medicinal agent to the water.

21. Apparatus for treating the respiratory gas of a subject, the subject having a tube in his/her respiratory tract through which a volume of respiratory gas is inhaled during an inhalation phase of a respiratory cycle and is exhaled during an exhalation phase of the respiratory cycle, the apparatus humidifying the respiratory gas inhaled by the subject and comprising:

a flow sensor for sensing the flow of respiratory gas;

measuring means coupled to said flow sensor for determining the respiratory gas volume associated with a given respiratory cycle of the subject, determining means for determining, from the measured respiratory gas volume, the amount of water that has been discharged from the subject during the exhalation phase of the respiratory cycle; and means for supplying water to respiratory gas inhaled by the subject, said means being coupled to said determining means for supplying, in a respiratory cycle subsequent to said given respiratory cycle, an amount of water dependent on the amount of water discharged from the subject to humidify the respiratory gas inhaled by the subject.

22. An apparatus according to claim 21 wherein said water supplying means is located downstream of said flow sensor in the direction of gas flow during inhalation.

23. An apparatus according to claim 21 wherein the water supplying means is further defined as supplying water during the inhalation phase of the respiratory cycle.

24. An apparatus according to claim 23 further including means coupled to said water supplying means for controlling the timing and duration of the water supply in the inhalation phase of the respiratory cycle.

25. An apparatus according to claim 21 wherein said determining means is further defined as controlling the water supplying means to supply an amount of water proportional to the amount of water discharged from the subject during the exhalation phase of the respiratory cycle.

26. An apparatus according to claim 21 wherein said water supplying means is further defined as spraying water into the respiratory gas inhaled by the subject.

27. An apparatus according to claim 21 wherein said water supplying means is further defined as supplying water in the form of an aerosol.

28. An apparatus according to claim 21 wherein said water supplying means is further defined as supplying water in the form of water vapor.

29. An apparatus according to claim 21 wherein said water supplying means includes a container, means for filling the container with the desired amount of water to be supplied in the subsequent respiratory cycle, and means for discharging the contents of the container until empty to supply the water to the respiratory gas of the subject.

30. An apparatus according to claim 29 wherein said water supplying means includes a cylinder comprising said container and a piston comprising said means for filling and discharging the contents of said cylinder.

31. An apparatus according to claim 21 further including means for heating the supplied water.

32. An apparatus according to claim 31 wherein said heating means is further defined as heating the respiratory gas into which the water is supplied.

33. An apparatus according to claim 21 further including means for measuring the temperature of the respiratory gas, said temperature measuring means being coupled to said determining means.

34. The apparatus according to claim 21 further including means for adding a medicinal agent to the water supplied to the respiratory gas.

35. An apparatus according to claim 21 further including a bacterial filter arranged in series with said flow sensor and said water supplying means.

36. An arrangement according to claim 21 further including a humidity and moisture exchanger arranged in series with said flow sensor and said water supplying means, said humidity and moisture exchanger recovering moisture and heat from exhaled respiratory gas and supplying same to inhaled respiratory gas.

* * * * *

UNITED STATES PATENT AND TRADEMARK OFFICE
CERTIFICATE OF CORRECTION

PATENT NO. : 5,964,219
DATED : October 12, 1999
INVENTOR(S) : Pekka Meriläinen

It is certified that error appears in the above-identified patent and that said Letters Patent is hereby corrected as shown below:

On the title page: Item [30]

Foreign Application Priority Data

Delete "962655" and substitute therefor ---962665---

Signed and Sealed this

Ninth Day of January, 2001

Attest:

Q. TODD DICKINSON

*Attesting Officer*     *Commissioner of Patents and Trademarks*